(12) United States Patent
Tsunoda et al.

(10) Patent No.: US 9,135,380 B2
(45) Date of Patent: Sep. 15, 2015

(54) METHOD FOR SIMULATING HIGH-VISCOSITY FLUID

(71) Applicant: Sumitomo Rubber Industries, Ltd., Kobe-shi, Hyogo (JP)

(72) Inventors: Masaya Tsunoda, Kobe (JP); Ryosuke Tanimoto, Kobe (JP); Arjun Yadav, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 220 days.

(21) Appl. No.: 13/867,479

(22) Filed: Apr. 22, 2013

(65) Prior Publication Data

US 2013/0332121 A1 Dec. 12, 2013

(30) Foreign Application Priority Data

Jun. 11, 2012 (JP) ................. 2012-132230

(51) Int. Cl.
*G06G 7/48* (2006.01)
*G06F 7/58* (2006.01)
*G06F 17/50* (2006.01)
*G06F 19/00* (2011.01)

(52) U.S. Cl.
CPC ............ *G06F 17/5018* (2013.01); *G06F 19/70* (2013.01); *G06F 2217/16* (2013.01)

(58) Field of Classification Search
CPC ................. G06F 17/5018; G06F 2217/16
USPC ............................... 703/2, 7, 9, 12
See application file for complete search history.

(56) References Cited

FOREIGN PATENT DOCUMENTS

JP  2011-27593 A  2/2011

OTHER PUBLICATIONS

Parvazinia, M., Nassehi, V., Wakeman, R. J., & Ghoreishy, M. H. R. (2006). Finite element modelling of flow through a porous medium between two parallel plates using the Brinkman equation. Transport in porous media, 63(1), 71-90.*
Ng, C. O., Chu, H. C., & Wang, C. Y. (2010). On the effects of liquid-gas interfacial shear on slip flow through a parallel-plate channel with superhydrophobic grooved walls. Physics of Fluids (1994-present), 22(10), 102002.*
Breuer et al., "Simulation and Visualization of Flow in a New Miniature Mixer of Multiphase Polymer Systems", Journal of Applied Polymer Science, vol. 97, No. 1, 2005, pp. 136-142.
Cheng et al., "Hydrodynamic Analysis of a Banbury Mixer-2-D Flow Simulations for the Entire Mixing Chamber", Polymer Engineering and Science, 1989, vol. 29, No. 15, pp. 1059-1065.
European Search Report dated Jul. 25, 2013 for Application No. 13 16 4282.
Ghoresihy et al., "Modeling the Transient Flow of Rubber Compounds in the Dispersive Section of an Internal Mixer with Slip-Stick Boundary Conditions", Advances in Polymer Technology, vol. 16, No. 1, 1997, pp. 45-68.

(Continued)

*Primary Examiner* — Aniss Chad
(74) *Attorney, Agent, or Firm* — Birch, Stewart, Kolasch & Birch, LLP

(57) ABSTRACT

A computerized method for simulating a high-viscosity fluid in a chamber is disclosed, wherein a model of the fluid is set in a model of the chamber and a flow calculation is performed. In the flow calculation, with respect to a contact surface of a wall of the chamber model with which the fluid model contacts, a slip velocity of the fluid model is defined by specific equations.

2 Claims, 10 Drawing Sheets

(56) References Cited

OTHER PUBLICATIONS

Hatzikiriakos, "Wall Slip of Molten Polymers", Progress in Polymer Science, vol. 37, No. 4, 2011, pp. 624-643.

Collin et al., "Numerical and Experimental Study of Dispresive Mixing of Agglomerates", Society of Plastics Engineers Annual Technical Conference, ANTEC 2006, Charlotte, NC, US, hal-00672092, Version 1, Feb. 20, 2012, 5 pages.

* cited by examiner

METHOD FOR SIMULATING HIGH-VISCOSITY FLUID

BACKGROUND OF THE INVENTION

The present invention relates to a computerized method for simulating a high-viscosity fluid.

In recent years, there have been proposed various computerized simulation methods including such a method in which a flow state of a plastic fluid such as uncrosslinked rubber or resin composite which is knead in a camber of a mixer such as banbury mixer is computed or simulated by calculating Navier-stokes equation.

[patent document 1] JP-A-2011-27593
[non-patent document 1] "Numerical and Experimental study of Dispersive Mixing of Agglomerates" V. Collin, E. Peuvrel-Disdier et al.

In the case of a flow calculation for a low-viscosity fluid such as air, the flow velocity of the fluid may be set at zero on the surface of a wall of a space where the fluid flows. However, in the case of a flow calculation for a high-viscosity fluid such as an uncrosslinked rubber composite not yet vulcanized, on the surface of a wall of a space where the fluid flows, the fluid may have a certain value of the flow velocity in the flow direction. Thus, the fluid slips on the wall. When making a computerized simulation for such a high-viscosity fluid, such slip phenomenon on a wall has to be taken into consideration.

Heretofore, the fluid velocity on a wall surface (hereinafter, slip velocity) is defined by a function of a shear stress on the wall surface. When the slip velocity is linear, the shear stress TW in accordance with Navie's Law is given by the following equation (1):

$$TW = F_{slip}[v_{slip} - v_{wall}] \quad (1)$$

and, when the slip velocity is nonlinear, the shear stress TW is given by the following equation (2):

$$TW = F_{slip}[v_{slip} - v_{wall}]|v_{slip} - v_{wall}|^{eslip-1} \quad (2)$$

wherein
"$v_{slip}$" is the velocity of the fluid on the wall surface in a direction parallel with the wall surface,
"$v_{wall}$" is a component of the moving velocity of the wall surface in a direction parallel with the wall surface,
"$F_{slip}$" is a user-defined invariable, and
"$e_{slip}$" is a user-defined invariable.

The value set to the invariable "$F_{slip}$" is specific to the fluid concerned and relates to the easiness of causing slip. Usually the value is determined through an experiment employing a device as disclosed in the patent document 1 for example. Through such experiment, the shear stress TW on a wall surface of a space in which the fluid flows, the slip velocity "$v_{slip}$" on the wall surface, and the moving velocity "$v_{wall}$" of the wall surface are measured.

Then, the value of "$F_{slip}$" is determined therefrom. More specifically, a double logarithmic chart, in which the slip velocity "$v_{slip}$" is plotted on the x-axis and the shear stress TW is plotted on the Y-axis, is prepared, and then a power approximation curve to the plotted points is found as $$y = a \cdot x^b.$$

The "$F_{slip}$" and "$e_{slip}$" are determined by the coefficient "a" and the power "b", respectively.

Then, the slip velocity ($v_{slip}$) on the wall surface is obtained by the following equation (3):

$$v_{slip} = v_{wall} + TW/F_{slip} \quad (3)$$

The obtained slip velocity ($v_{slip}$) is given to a solver, and according thereto, the solver performs a convergent calculation to obtain solution.

If the value of the invariable "$F_{slip}$" is small or the value of the shear stress TW is abnormal, then the value of the slip velocity "$v_{slip}$" obtained from the equation (3) and given to the solver becomes abnormal.

Thus, if the slip velocity is introduced in the conventional fluid simulation method, there is a possibility that the computation becomes uncertain such that the iterative calculation is not converged or diverges.

SUMMARY OF THE INVENTION

It is therefore, an object of the present invention to provide a computerized method for simulating a high-viscosity fluid in which a flow calculation of the high-viscosity fluid becomes stable, and it is possible to accurately simulate flowing states of the high-viscosity fluid.

According to the present invention, a computerized method for simulating a high-viscosity fluid in a chamber with a wall, comprises:
a step in which a chamber model of the chamber is defined,
a step in which a fluid material model of the fluid is defined, and
a step in which the fluid material model is set in the chamber model and a flow calculation is performed under predetermined conditions,
wherein
in the flow calculation, with respect to a contact surface of the wall of the chamber model with which the fluid material model contacts, a slip velocity "$v_{slip}$", which is a velocity of the fluid material model in a direction parallel with the contact surface, is defined by the following equation (a)

$$v_{slip} = \alpha \cdot v_t + (1 - \alpha) \cdot v_{wall} \quad (a)$$

wherein
"$v_t$" is a component of the velocity of the fluid material model in a direction parallel with the contact surface at a position spaced apart from the contact surface by a distance "$d_{wall}$" normally thereto,
"$v_{wall}$" is a component of a velocity of the contact surface in a direction parallel with the contact surface, and
"$\alpha$" is a slip ratio as a variable from 0 to 1,
wherein
the "$\alpha$" satisfies the following equation (b) or (c)

$$\alpha/(1-\alpha) = \mu/(d_{wall} \cdot F_{slip}) \quad (b)$$

$$\alpha/(1-\alpha) = \mu/\{(d_{wall} \cdot F_{slip})|v_{slip} - v_{wall}|^{eslip-1}\} \quad (c)$$

wherein
"$\mu$" is the viscosity of the fluid material model,
"$F_{slip}$" is an invariable, and
"$e_{slip}$" is an invariable.

For example, the chamber is a kneading space of a banbury mixer defined between a casing of the banbury mixer and at least one rotor rotatably disposed in the casing, and the fluid is uncrosslinked rubber or resin material to be kneaded with the rotor or rotors.

Therefore, the slippage of the fluid on the wall is reckoned in the flow calculation. Accordingly, an accurate simulation of a flow of a high-viscosity fluid such as uncrosslinked rubber or resin is possible.

when the slip ratio "$\alpha$" is 0 in the equation (a), the slip velocity "$v_{slip}$" becomes equal to the velocity "$v_{wall}$" of the contact surface. When the velocity "$v_{wall}$" is 0, the velocity of the fluid material model becomes 0. This corresponds to a state in which a slippage of the fluid material model does not occur on the contact surface.

when the slip ratio "α" is 1 in the equation (a), the slip velocity "$v_{slip}$" becomes equal to the velocity "$v_t$" of the fluid material model in a direction parallel with the contact surface at a position spaced apart from the contact surface by a distance "$d_{wall}$" normally thereto. This corresponds to a state in which the fluid material model fully slips on the contact surface, in other words, there is no friction therebetween.

According to the present invention, the slip velocity "$v_{slip}$" can be stably computed, therefore, it is possible to certainly converge the flow calculation performed in the simulation.

DESCRIPTION OF THE PREFERRED EMBODIMENTS

Embodiments of the present invention will now be described in detail in conjunction with accompanying drawings.

The present invention is directed to a method for simulating flow states of a fluid flowing in a chamber by the use of a computer (not shown).

Here, the target fluid is a high-viscosity fluid such that a relatively large slip occurs on the contact surface of a wall of the chamber. For example, plastic materials such as uncrosslinked rubber, resin and elastomer correspond thereto on the assumption that the plastic material is sufficiently kneaded and well mixed and thereby being in a state such that stable flows of the plastic material occur. In particular, the rubber whose temperature is increased to about 80 degrees C. may be considered as being in such state.

The chamber is a space which is enclosed by wall surfaces and in which the high-viscosity fluid is moved. The chamber may have various shapes or configurations. A typical chamber is a kneading space of a banbury mixer in which materials are kneaded and mixed.

Figure 1:
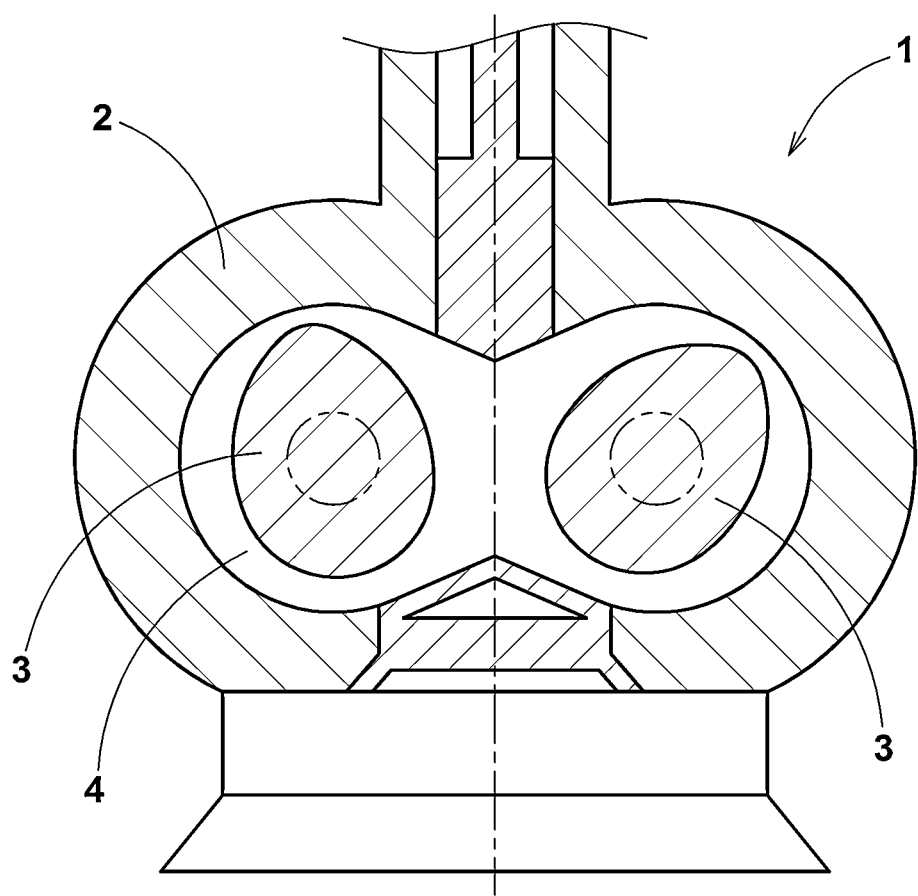
FIG. 1 is a cross sectional view of an essential part of a banbury mixer for kneading a plastic material.

FIG. 1 shows a schematic cross section of a banbury mixer 1.

The banbury mixer 1 in this example comprises a casing 2, a pair of rotors 3 rotatably disposed in the casing 2, and a chamber 4 formed between the casing 2 and two rotors 3 as a kneading space having a shape of the figure of 8. Of course the chamber 4 may have a variety of shapes other than the figure of 8.

Figure 2:
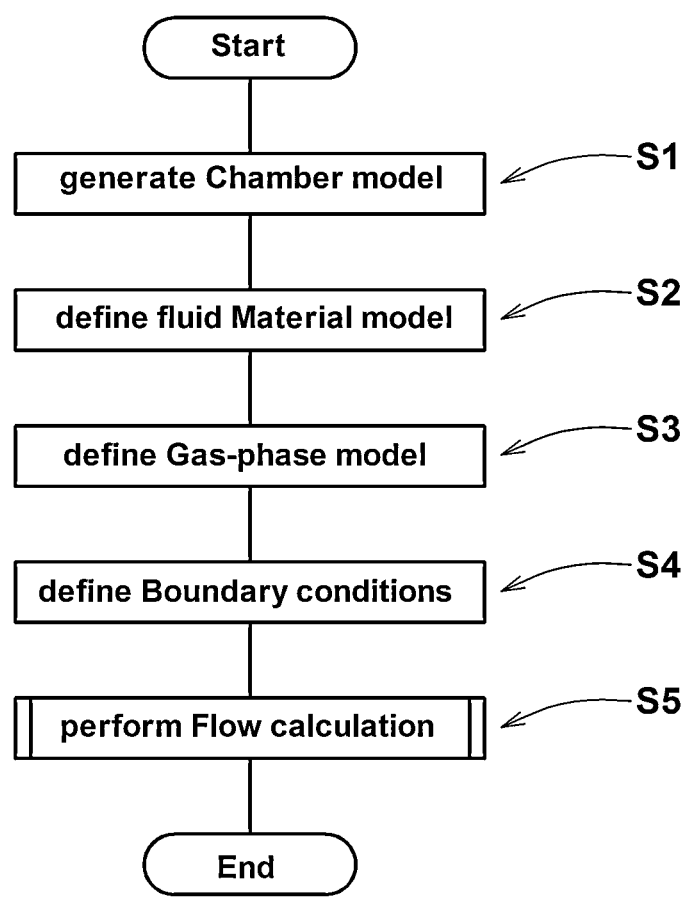
FIG. 2 is a flow chart of a fluid simulation method as an embodiment of the present invention.

FIG. 2 shows a flowchart of a simulation method as an embodiment of the present invention.

*Step S1 of Defining Chamber Model

According to the simulation method in this embodiment, firstly, a chamber model which is a finite element model of the chamber 4 is defined and stored in the computer.

Figure 3:
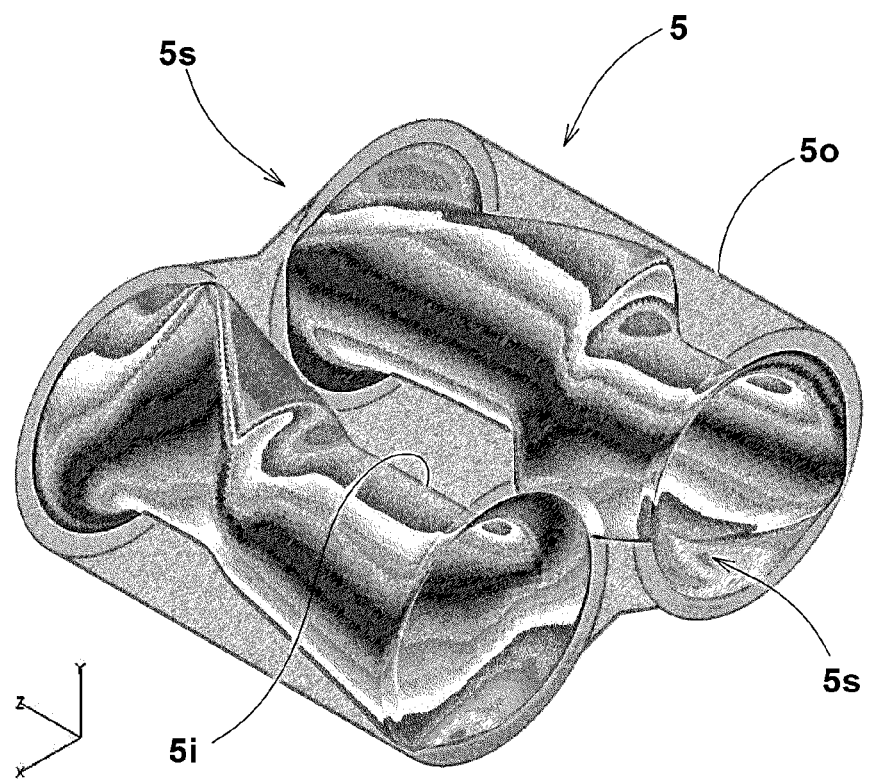
FIG. 3 shows a chamber model rendered as a perspective view.
Figure 4:
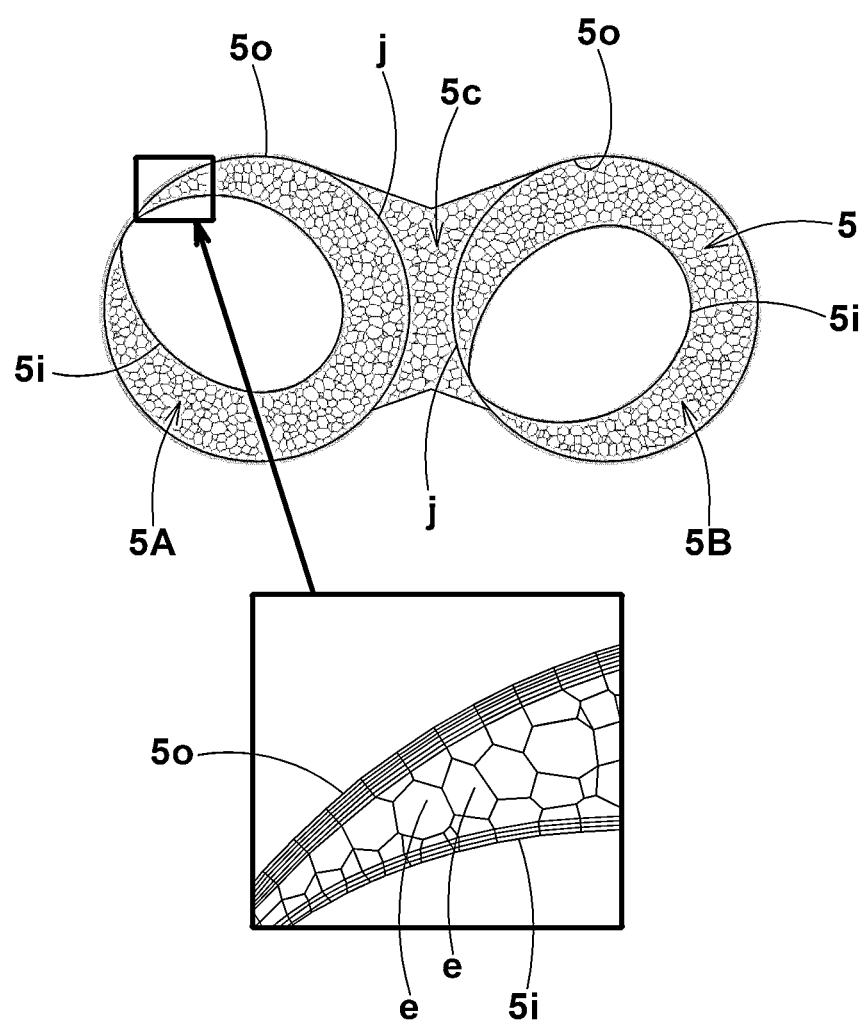
FIG. 4 shows a cross section of the chamber model.

FIG. 3 shows the chamber model 5 rendered as a perspective view. FIG. 4 shows a cross section thereof.

The chamber model 5 is a three-dimensional space which is divided into a finite number of three dimensional elements (e) and which is enclosed by its own outside circumferential surface 5o formed by the inside circumferential surface of the casing 2, its own inside circumferential surface 5i formed by the outside circumferential surfaces of the respective rotatable rotors 3, and its own end surfaces 5s on both sides in the axial direction of the rotors 3.

The surfaces 5o, 5i and 5s are the above-mentioned wall surfaces of the chamber model 5.

The above-mentioned three dimensional elements (e) of the chamber model 5 are Euler elements. For example, one kind or plural kinds of polyhedral elements such as tetrahedral elements and hexahedral elements are used.

As explained afterward, with respect to each of the elements (e), physical quantities of the plastic material (fluid material model), e.g. pressure, temperature, velocity and the like are computed.

The outside circumferential surface 5o and end surfaces 5s of the chamber model 5 are defined as being not deformable.

The inside circumferential surface 5i of the chamber model 5 is defined as being not deformable and rotatable in accordance with the rotation of the rotors 3 to allow a change in the shape of the chamber model 5.

Figure 5:
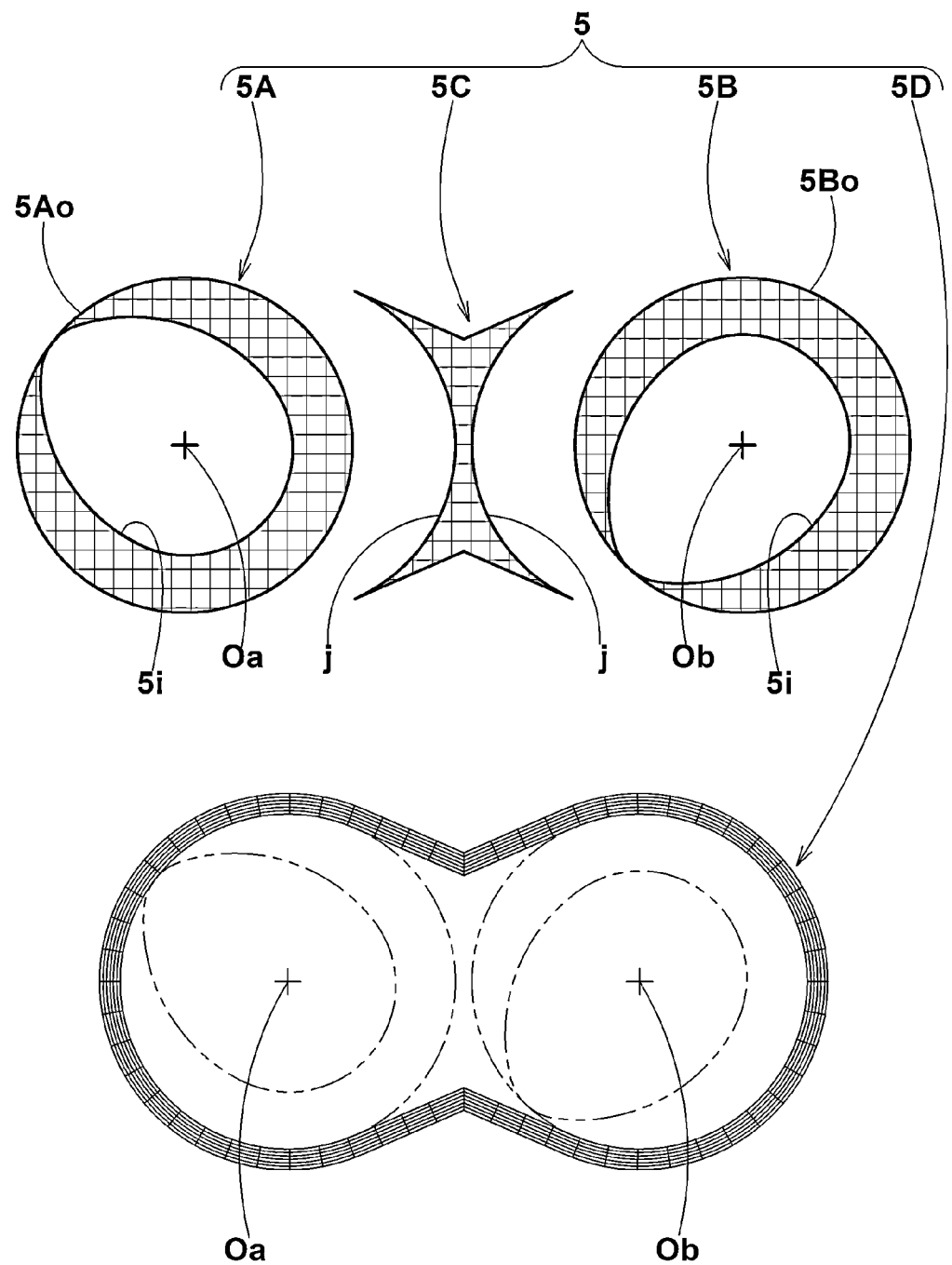
FIG. 5 is a cross section of the chamber model divided into functional parts.

In this embodiment, in order to effectively simulate the change in the shape of the chamber model 5, the chamber model 5 is divided into four parts which are, as shown in FIG. 5, a pair of rotative parts 5A and 5B, a connecting part 5C therebetween, and an outer frame part 5D encompassing the above-mentioned parts 5A, 5B and 5C.

Each rotative part 5A/5B is tubular and has a cylindrical outside circumference surface 5Ao/5Bo and an inside circumferential surface 5i corresponding to the outside circumference surface of one rotor 3.

The rotative parts 5A and 5B are placed in the outer frame part 5D and defined as rotatable around the respective center axes Oa and Ob to represent the change in the configuration of the volume of the chamber 3 caused by the rotations of the rotors 3.

In contrast, the in-between connecting part 5C remains at rest between the rotative parts 5A and 5B, and has two concave surfaces j abutting on the respective rotative parts 5A and 5B.

On the concave surfaces j and the respective cylindrical outside circumference surfaces 5Ao and 5Bo, boundary conditions as sliding surface are defined. This allows physical actions (force, heat, etc.) occurring in the rotative parts 5A and 5B to be transferred to the fluid model existing in the in-between connecting part 5C through the concave surfaces j.

The outer frame part 5D is tubular and surrounds the rotative parts 5A and 5B and the in-between connecting part 5C. Both of the axial ends thereof are closed by the two end surfaces 5s.

On the interface between the outer frame part 5D and the rotative parts 5A and 5B, and also on the interface between the outer frame part 5D and the in-between connecting part 5C, boundary conditions as sliding surface are defined. This allows physical actions (force, heat, etc.) occurring in the rotative parts 5A and 5B to be transferred to the outer frame part 5D through the interfaces therebetween.

The outer frame part 5D is subjected to a relatively large shearing force by the operation of the rotors. Therefore, in order to calculate the velocity and the like of the material in more detail, it is preferred that the elements constituting the outer frame part 5D are made smaller in size than those of the rotative parts 5A and 5B and the in-between connecting part 5C. Thereby, velocity profile and the like of the fluid material model near the interior surface of the chamber model 5 can be calculated in more detail.

*Step S2 of Defining Fluid Model

Next, the fluid material model is defined by the computer and stored.

The fluid material model is a model of the fluid (plastic material) flowing or moving in the chamber 4.

On the fluid material model, physical properties of the plastic material such as shear viscosity, specific heat, thermal conductivity and specific gravity are defined and stored in the computer.

As to the shear viscosity, the analysis object (plastic material) are measured for viscoelastic properties G' and G" under a plurality of temperature conditions, and by converting the viscoelastic properties according to the Cox-Merz rule, the shear viscosity is obtained.

The shear viscosity μ obtained as above is approximated by the following equation (4) according to a power law.

$$\mu = m\gamma'^{n-1} \quad (4)$$

wherein
m: a coefficient as a function of absolute temperature T,
γ': a shear velocity, and
n: a coefficient.

As to the specific heat of the fluid material model, the plastic material as the analysis object is measured by a thermally-insulated continuous-heating method (@ 25 degrees C.), and the measured specific heat value is entered and stored in the computer in advance.

As to the thermal conductivity of the fluid material model, the plastic material as the analysis object is measured by a hot wire method (@ 25 degrees C.), and the measured value is entered and stored in the computer in advance.

*Step S3 of Defining Gas-Phase Model

Next, a gas-phase model is defined by the computer and stored.

The gas-phase model is a model of gas existing in the chamber as a second fluid.

In this embodiment, the filling rate of the plastic material in the chamber is less than 100%. Therefore, in order to enable flow calculations, the part of the chamber model 5 not filled with the fluid material model, is filled with the gas-phase model.

On the gas-phase model, viscosity and specific gravity of the gas are defined and stored in the computer.

Usually, the actual values of the viscosity and specific gravity of air at a certain temperature are set to the gas-phase model. But, values different from the actual values may be set.

When making an analysis of a multiphase flow of the gas-phase model (air) and fluid material model (plastic material) having largely different viscosities, there is a possibility that the shear heat generation is increased at the interface between the gas-phase model and fluid material model, and thereby the flow calculation becomes unstable.

In this embodiment, in order for the stable flow calculation, the value of the viscosity set to the gas-phase model is increased as much as possible from the actual value as far as it does not exert a bad influence on the calculated result.

The present inventors made flow calculations (flow simulations) under different conditions where only the value of the viscosity set to the gas-phase model was changed in order to compare the pressure field in the chamber model 5.

As a result, it was discovered that, if the vale of the viscosity of the gas-phase model exceeds 10 times the actual value of the viscosity of air, the value of the pressure in the chamber model 5 is increased and exerts a bad influence on the pressure field.

On the other hand, if the vale of the viscosity of the gas-phase model is lower than 5 times the actual value of the viscosity of air, it is difficult to completely prevent the flow calculation from becoming unstable.

Therefore, values within a range of from 5 to 10 times the actual vale of the viscosity of the air may be preferably set to the gas-phase model.

*Step S4 of Defining Boundary Conditions

Next, various conditions necessary for carrying out the flow calculation such as boundary conditions are defined.

The boundary conditions include flow velocity boundary conditions and temperature boundary conditions on the wall surface of the chamber model 5.

As to the flow velocity boundary conditions, a contact part of the wall surface of the chamber model 5 with which the fluid material model contacts, is provided with wall-surface slip conditions such that the fluid material model may have a certain velocity or slip velocity in the contact part during the flow calculation.

As to the temperature boundary conditions,
(a) thermally insulated condition in which the heat does not escape outside from the chamber model 5 through the surface thereof, or
(b) condition in which the entire surface of the chamber model 5 has a constant temperature (for example 50 degrees C.)
may be defined according to the purpose of the simulation, required accuracy and the like.

Further, the conditions may include the initial temperature of the fluid material model. In this embodiment, the initial temperature is set to 20 degrees C.

Furthermore, the conditions may include the numbers of rotations of the rotative parts 5A and 5B of the chamber model corresponding to the number of rotations of the rotors of the banbury mixer.

Still furthermore, the conditions may include the filling rate of the fluid material model to the entire volume of the chamber model 5.

Further, an initial state of the flow calculation, time intervals for calculations, the number of iterations in the internal processing, the maximum period of computation (iteration) and the like may be included as the conditions.

Figure 6:
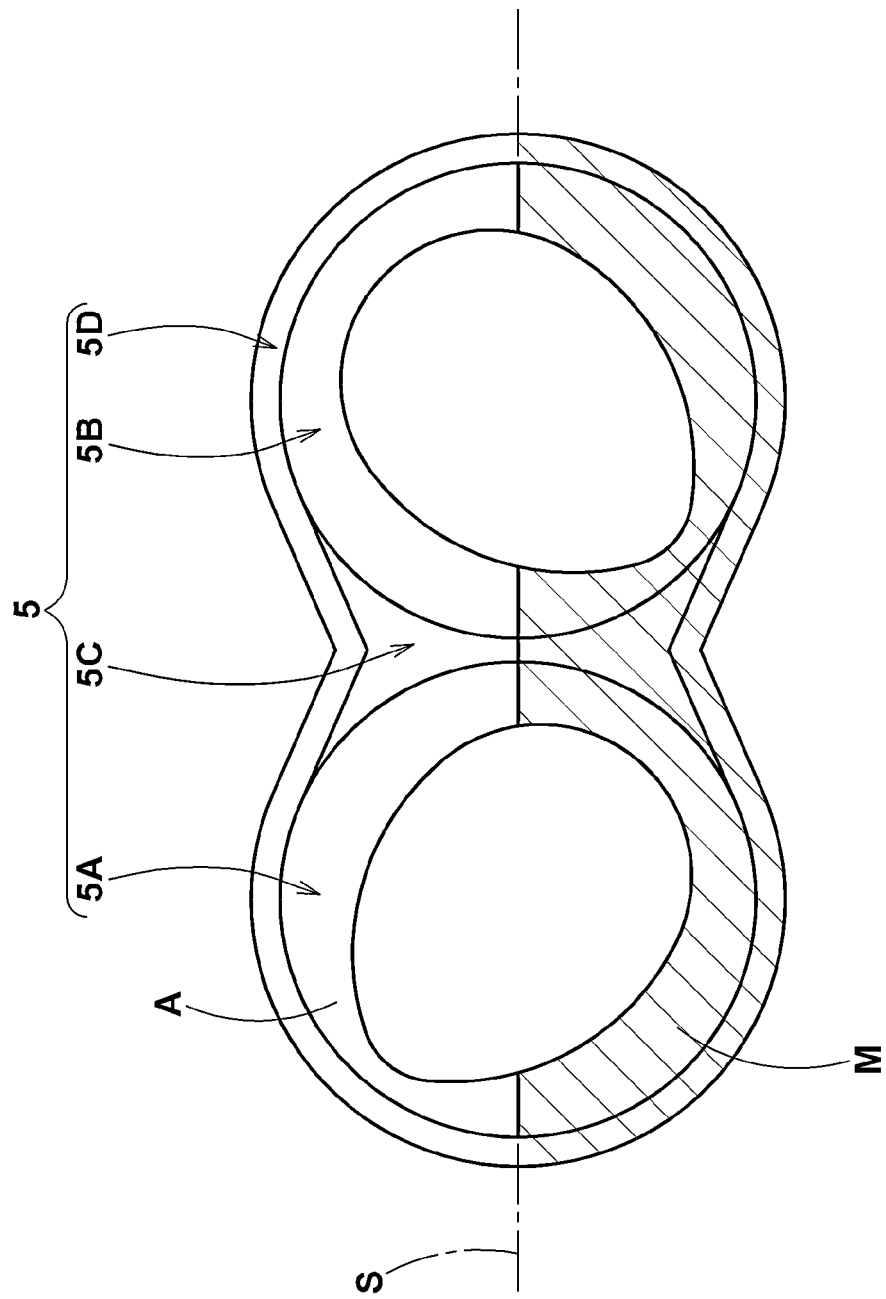
FIG. 6 is a schematic cross sectional view showing a state of the chamber model in which a fluid material model and a gas-phase model are arranged.

As to the initial state, for example as shown in FIG. 6, it is possible to define such that
the domain A on the upper side of a horizontal interface S defined as extending across the chamber model 5 is of the gas-phase model, and
the domain M on the under side of the horizontal interface S is of the fluid material model.

Therefore, by changing the level of this interface S, the filling rate of the fluid material model (plastic material) can be adjusted.

*Step S5 of Performing Flow Calculation

In this embodiment, as shown in FIG. 6, the fluid material model (domain M) and gas-phase model (domain A) are set in the chamber model 5, and the flow calculation is performed according to the conditions defined as above.

In the flow calculation, at least the following five unknown quantities are computed, namely, three components of the velocity in three coordinate axis directions (x, y and z directions) of the fluid material model and the pressure p and temperature T of the fluid material model.

In this embodiment, the flow calculation is made based on Navier-stokes equation for incompressibility flows. Thus, during the flow calculation, the densities of the gas-phase model and fluid material model are treated as being constant.

In this embodiment, the fluid material model is treated as being fluid throughout the entire temperature range during the flow calculation. Thus, the fluid equation to be solved is simultaneous equations (Navier-stokes equation, mass conservation equation and energy equation).

In the flow calculation in this embodiment, it is necessary to simultaneously deal with the two kinds of fluid which are the gas-phase model and the fluid material model existing in the chamber model 5.

For this purpose, in this embodiment, the VOF (volume of Fluid) method, which is used to calculate a flow with a free interface, is employed.

The VOF method does not directly calculate the motion of the interface between two kinds of fluid. In the VOF method, a free interface is expressed by defining a volume fraction which corresponds to a filling rate of the fluid material model within the volume of each element of the chamber model 5.

The government equations are as follows.

*[Motion Equation]

In this embodiment, a two-phase flow in which the gas-phase model and the fluid material model flow together in the chamber model 5 is treated as a single phase flow. In such case, the motion equation to be solved is the following equation (5) in the three coordinate axes directions x, y and z. This becomes possible as a result of that the two phases are averaged by the VOF method and treated as a single phase.

$$\frac{\partial}{\partial t}(\rho \vec{u}) + \nabla \cdot (\rho \vec{u}\vec{u}) = -\nabla p + \nabla \cdot [\mu(\nabla \vec{u} + \nabla \vec{u}^T)] + \rho \vec{g} + \vec{F} \quad \text{Equation (5)}$$

wherein
u: velocity of the multiphase flow model,
p: pressure of the multiphase flow model,
ρ: density of the multiphase flow model,
g: gravitational acceleration,
T: absolute temperature of the multiphase flow model,
F: external force.

The values of the density ρ and coefficient of viscosity μ of an element including the fluid material model and the gas-phase model are weighted by the occupied volumes of the respective phases (namely, the material model and gas-phase model) and then averaged as shown in the following equation (6).

$$\rho = \Sigma \delta_q \rho_q \quad \mu = \Theta \delta_q \mu_q \quad \text{Equation (6)}$$

wherein
$\delta_q$: volume fraction
$\rho_q$: density of each phase in each element
$\mu_q$: viscosity of each phase in each element

*[Mass Conservation Equation]

As to the mass conservation equation (equation of continuity) and pressure equation, it is enough to solve only one set of equations in the three coordinate axes directions. Therefore, according to the simulation method in this embodiment, the computer can calculate the flow field as a shingle phase despite the multiphase. In other words, to be solved is the flow in which the materials properties are varied with position (volume fraction).

The position of each phase can be estimated according to the distribution of the volume fraction obtained as the result of the calculation.

*[Energy Equation]

The temperature of the fluid material model can be obtained by the following energy equation (7).

$$\frac{\partial}{\partial t}(\rho E) + \nabla \cdot (\vec{u}(\rho E + p)) = \nabla \cdot (k_{\text{eff}} \nabla T) + S_h \quad \text{Equation (7)}$$

$$E = \frac{\sum_{q=1}^{n} \delta_q \rho_q E_q}{\sum_{q=1}^{n} \delta_q \rho_q}$$

wherein
E: enthalpy,
k: thermal conductivity, and
S: source term.

*[Transport Equation of Volume Fraction]

The distribution of the volume fraction determines the position of the interface between the two phases (or the gas-phase model and material model).

The volume fraction $\delta_q$ can be obtained by accurately solving the following equation (8).

$$\frac{\partial}{\partial t}(\delta_q \rho_q) + \nabla \cdot (\delta_q \rho_q \vec{u}_q) = S_{\delta q} \quad \text{Equation (8)}$$

If the volume fraction $\delta_q$ equals 0 in an arbitrary element (e) of the chamber model 5, this means that the q phase (q phase=fluid material model) does not exist in this element (e).

If the volume fraction $\delta_q$ equals 1, this means that the entire volume of the element (e) is filled with the q phase.

If $0 < \delta_q < 1$, this means that the element (e) is filled with the q phase (fluid material model) and other phase (gas-phase model), that is, the element is multiphase having an interface.

This equation can be solved by Modified-HRIC (Implicit) of which detailed description is given by "ANSYS Fluent user's Manual, 26.2.9 Modified HRIC scheme."

In this embodiment, each of the above-mentioned equations is solved by the pressure-based partitioned method.

For the coupling of the pressure equation and the motion equation, the SIMPLE (semi-Implicit Method for Pressure-Linked Equations) algorithm is preferably used.

Figure 7:
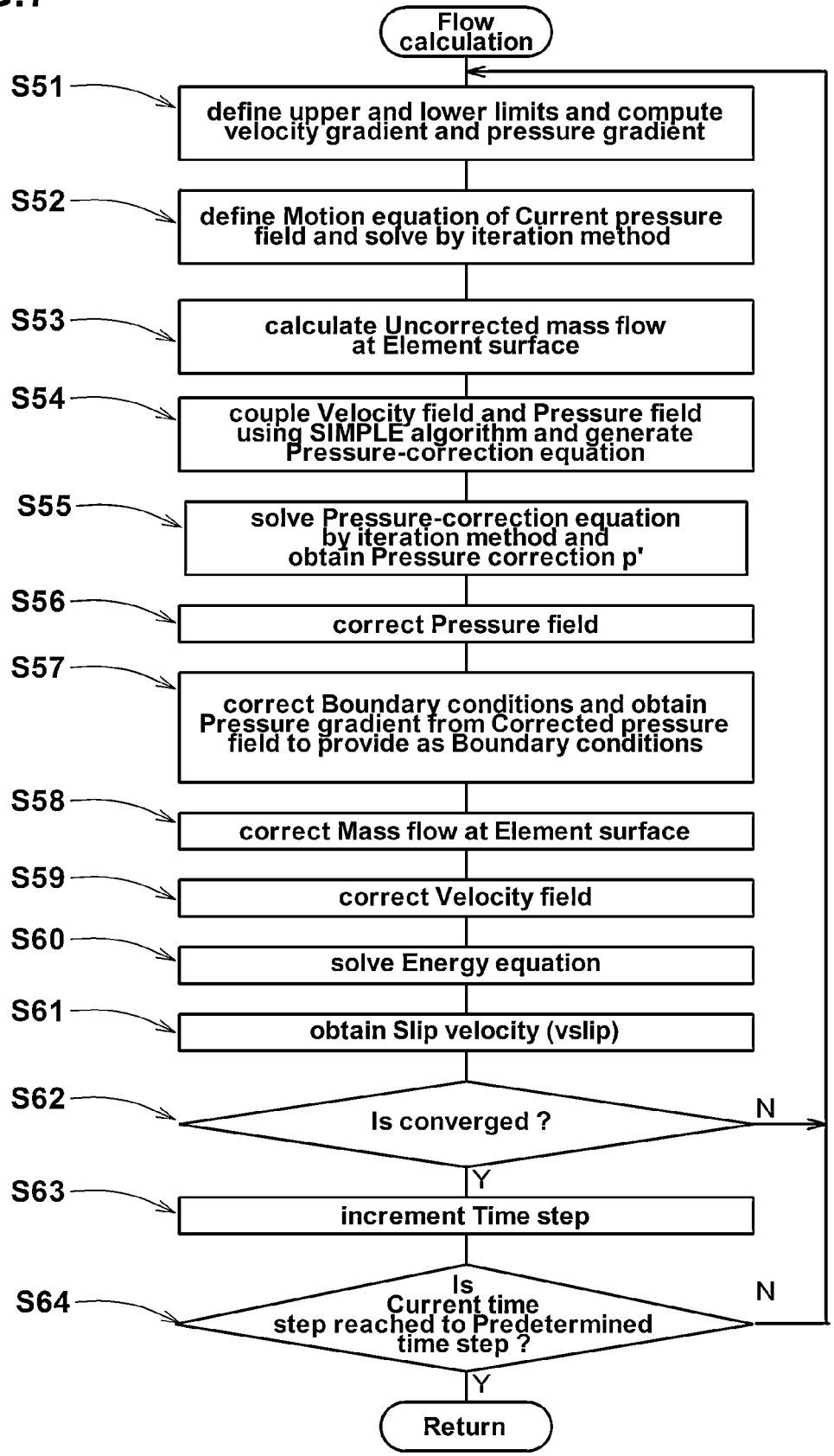
FIG. 7 is a flow chart of a flow calculation.

FIG. 7 shows a flowchart of an example of the flow calculation performed by the computer.

** Step S51

In this example, firstly, upper and lower limits for the pressure gradient and the velocity are set, and the velocity gradient and the pressure gradient are computed.

** Step S52

Next, the motion equation is defined by discretization of the current pressure field, and the motion equation is solved by a method of iteration. That is, the velocity of the material model (or multiphase) in three coordinate axes directions is computed. As to the method of iteration, the Gauss-Seidel method can be used.

** Step S53

Next, in order to examine whether or not the above-mentioned velocity satisfies the equation for conservation of mass, uncorrected mass flow of the fluid material model on the surfaces of the elements of the chamber model 5 is calculated first.

Here, the "uncorrected mass flow" is a mass flow temporarily used at the beginning of the loop of the SIMPLE algorithm. Such mass flow may have a large error, therefore, it is called "uncorrected mass flow".

The mass flow of an element is the flow of the mass of a substance concerned which passes through the entire surface of the element concerned.

** Step S54

Next, using the SIMPLE algorithm, the velocity field and the pressure field are coupled, and the following pressure-correction equation (9) for correcting the pressure field is generated.

$$\nabla[k\nabla\phi] = src \quad \text{Equation (9)}$$

** Step S55

Next, by the method of iteration for example AMG solver, CG or Bi-CG and the like, the pressure-correction equation is solved, and a pressure correction amount p' is computed.

** Step S56

Next, based on the obtained solution, the pressure field is corrected by the following equation (10):

$$p^{n+1} = p^n + \omega p' \quad (10)$$

wherein
p: pressure,
n: current number of time step, and
ω: relaxation coefficient.

In this example, 0.3 is set to the relaxation coefficient, but another value may be set thereto.

** Step S57

Next, the boundary conditions of the interfaces are corrected (or updated). Here, the interfaces are those between the fluid models including the fluid material model and gas-phase model and the other solid models (rotor and chamber). Specifically, from the corrected pressure field, the pressure gradient is obtained. The obtained pressure gradient is provided as the boundary conditions.

** Step S58

Next, the mass flow at the surfaces of the elements is corrected by the following equation (11):

$$m_f^{n+1} = m_{f*} + m'_f \quad (11)$$

wherein,
$m_f^{n+1}$: corrected mass flow at the surfaces of the elements,
$m_{f*}$: uncorrected mass flow at the surfaces of the elements,
$m'_f$: correcting value of mass flow.

** Step S59

Next, the velocity field is corrected by the following equation (12):

$$v^{n+1} = v^* - (v\nabla p'/\partial_p V) \quad (12)$$

wherein
v: volume of element,
v*: intermediary velocity field before corrected, obtained from motion equation,
$\partial_p V$: diagonal component of matrix of motion equation, and
$\nabla p'$: gradient of pressure correction amount.

** Step S60

Next, by solving the above-mentioned energy equation (7), the temperature and viscosity of the material model are calculated.

** Step S61

Further, the slip velocity "$v_{slip}$" of the wall-surface of the chamber model 5 is calculated by the equation (a):

$$v_{slip} = \alpha \cdot v_t + (1-\alpha) \cdot v_{wall}$$

Figure 8:
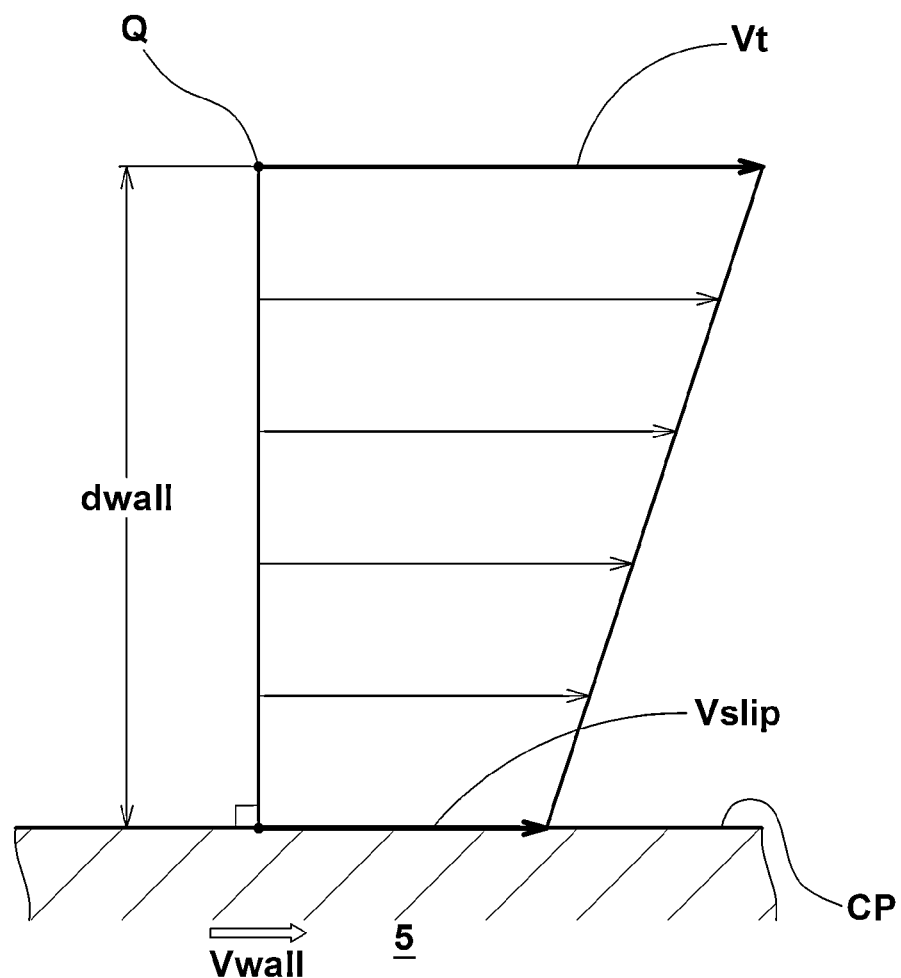
FIG. 8 is a diagram for explaining the velocity of the fluid material model flowing near the wall surface.

As shown in FIG. 8, in the equation (a),
"$v_t$" is a component of the velocity of the fluid material model in a direction parallel with the contact surface CP of the chamber model at a position spaced apart from the contact surface CP by a distance "$d_{wall}$" normally thereto,
"$v_{wall}$" is a component of the velocity of the contact surface CP in a direction parallel with the contact surface CP
"α" is the slip ratio which is a variable from 0 to 1.

When the slip velocity is linear as shown in FIG. 8, the slip ratio "α" satisfies the following equation (b).

When the slip velocity is nonlinear (not shown), the slip ratio "α" satisfies the following equation (c).

$$\alpha/(1-\alpha) = \mu/(d_{wall} \cdot F_{slip}) \quad \text{Equation (b)}$$

$$\alpha/(1-\alpha) = \mu/\{(d_{wall} \cdot F_{slip})|v_{slip} - v_{wall}|^{e_{slip}-1}\} \quad \text{Equation (c)}$$

In the equations (b) and (c),
"μ" is the viscosity of the fluid material model,
"$F_{slip}$" is an invariable, and
"$e_{slip}$" is an invariable.

In accordance with "Computational Methods For Fluid Dynamics", P256-P257, equations (8.74) and (8.75) (authors: Joel H. Ferziger and Milovan Peric, publisher: Springer), when the slip velocity is linear, the shear stress TW at the contact surface CP is generically given by the following equation (13).

$$\tau_\omega = \mu\left[\frac{v_t - v_{slip}}{d_{wall}}\right] \quad \text{Equation (13)}$$

From the equation (1) and equation (13), we obtain the following equation (14).

$$\mu\left[\frac{v_t - v_{slip}}{d_{wall}}\right] = F_{slip}[v_{slip} - v_{wall}] \quad \text{Equation (14)}$$

Introducing the equation (a) in the equation (14), we obtain the equation (15).

$$\left[\frac{\mu(1-\alpha)}{d_{wall}}\right] = F_{slip}\alpha \quad \text{Equation (15)}$$

The equation (15) can be written as the equation (b). In the equation (15) or (b),
"μ" is the value of the viscosity of the fluid material model which is specific thereto,
"$d_{wall}$" is a known value. For example, the distance from the contact surface CP to the center (representative point) of an element abutting the contact surface CP may be set as the "$d_{wall}$". In this case therefore, the value of the "$d_{wall}$" is determined by the meshing of the chamber model 5.

In the equation (b), "$F_{slip}$" is a user-defined known invariable. Accordingly, the slip ratio "a" can be easily determined from the equation (b).

The slip velocity "$v_{slip}$" can be easily obtained by introducing the slip ratio "α" into the equation (a).

By utilizing such equations, it can be avoided that the slip velocity "$v_{slip}$" of the fluid material model shows an abnormal value. Accordingly, the robustness of the fluid simulation is improved, and the deterioration of the accuracy due to the shoot-up velocity can be prevented. Further, the convergence of the calculation can be improved to shorten the computational time.

when the slip velocity is nonlinear, from the equation (2) and equation (13), we obtain the following equation (16).

$$\mu\left[\frac{v_t - v_{slip}}{d_{wall}}\right] = F_{slip}[v_{slip} - v_{wall}]|v_{slip} - v_{wall}|^{eslip-1} \quad \text{Equation (16)}$$

From the equation (16) and equation (a), we obtain the above-mentioned equation (c).

When the difference between the slip velocity "$v_{slip}$" and the velocity "$v_{wall}$" on the contact surface is very small, the value of a denominator of the equation (c) becomes very small. In this case, accordingly, there is a possibility that so called "division by zero" is caused during the calculation of the equation (c).

Therefore, in the case that the nonlinear slip velocity is defined, when the value of the velocity difference ($v_{slip}-v_{wall}$) in the equation (c) becomes less than a predetermined threshold (for example, about $1.0 \times 10^{-8}$), it is desirable to use the equation (b) in order to make a stable calculation based on the nonlinear slip velocity.

Figure 9:
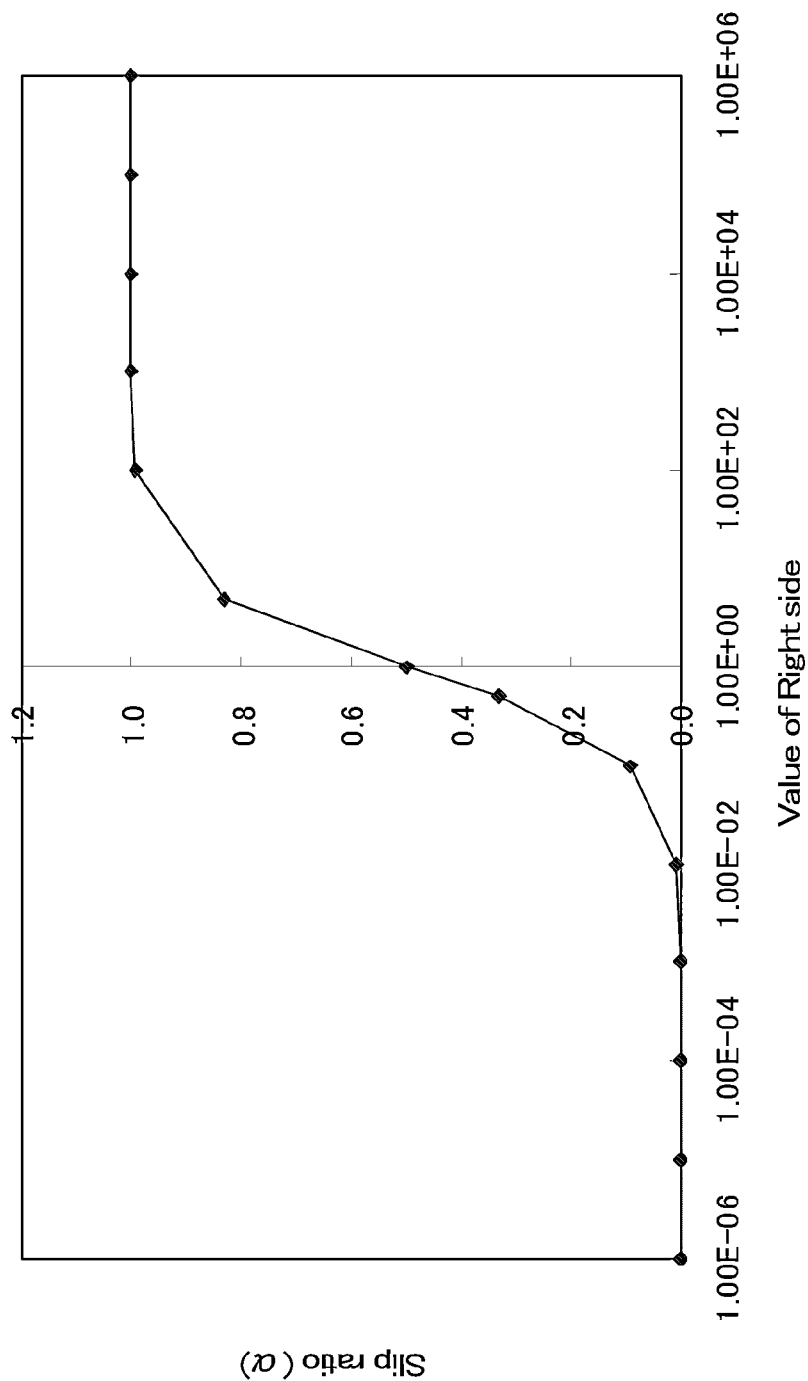
FIG. 9 is a graph showing a relationship between the value of the slip ratio and the value of the right side of the equation (b) or (c).

FIG. 9 is a graph showing a relationship between the value of the right-hand side of the equation (b) or (c) and the value of the slip ratio "$\alpha$".

Even if the value of the right-hand side which is always positive, is largely varied, the range of the variation of the value of the slip ratio "$\alpha$" is between 0 and 1.

Therefore, according to the present invention, if the equation (b) is used, the slip ratio "$\alpha$" never have abnormal values.

** Step S62

Next, it is judged if the solution of this calculation is converged. Here, the solution is of the Navier-Stokes equation (equation (5)+Equation of continuity) as the government equation of the fluid simulation in this embodiment.

The convergence can be judged, based on whether the total number of the corrected mass flows is within a predetermined error range or not.

If judged as being not converged (N in step S62), then the computer again performs the step S51 and subsequent steps.

** Step S63

If judged as being converged (Y in step S62), the time step is incremented by one to put a clock forward by one time interval.

** Step 64

Further, it is judged if the current time step is not reached to the predetermined time step.

If the current time step is not reached to the predetermined step time (N in step S64), then the computer again performs the step S51 and subsequent steps.

In the flow calculations in this embodiment, the shear heating of the fluid material model is calculated, but the shear heating of the gas-phase model is not calculated.

The shear heat generation of the fluid material model has to be considered because of the plastic material.

The shear velocity often becomes increased at the interface between the fluid material model and the gas-phase model.

The shear heat generation corresponds to the product of the shear viscosity and the square of the shear velocity, therefore, if the value of the shear velocity is extremely large, there is a possibility that the calculation of the temperature (energy equation) is adversely affected.

So, in this embodiment, the calculation of the shear heat generation is limited to only the fluid material model, more particularly to only the elements whose volume fraction $\delta_q$ is not less than a constant value (in this embodiment, 0.90) in order to make the calculation stable.

Comparison Tests

In order to confirm the advantageous effects of the present invention, using the chamber model shown in FIG. 3 and the fluid material model of unvulcanized rubber, a simulation of kneading continued for a real time of 20 seconds was made according to the above-described method, wherein the filling rate of the unvulcanized rubber in the chamber model was 70%, the number of rotations of the rotors was 30 rpm, and the computational time interval was $1.973 \times 10^{-3}$ seconds.

During computing the slip velocity by the use of the equations (a) and (b), an abnormal value of the slip velocity did not occur, and the flow calculation was stably converged.

Figure 10:
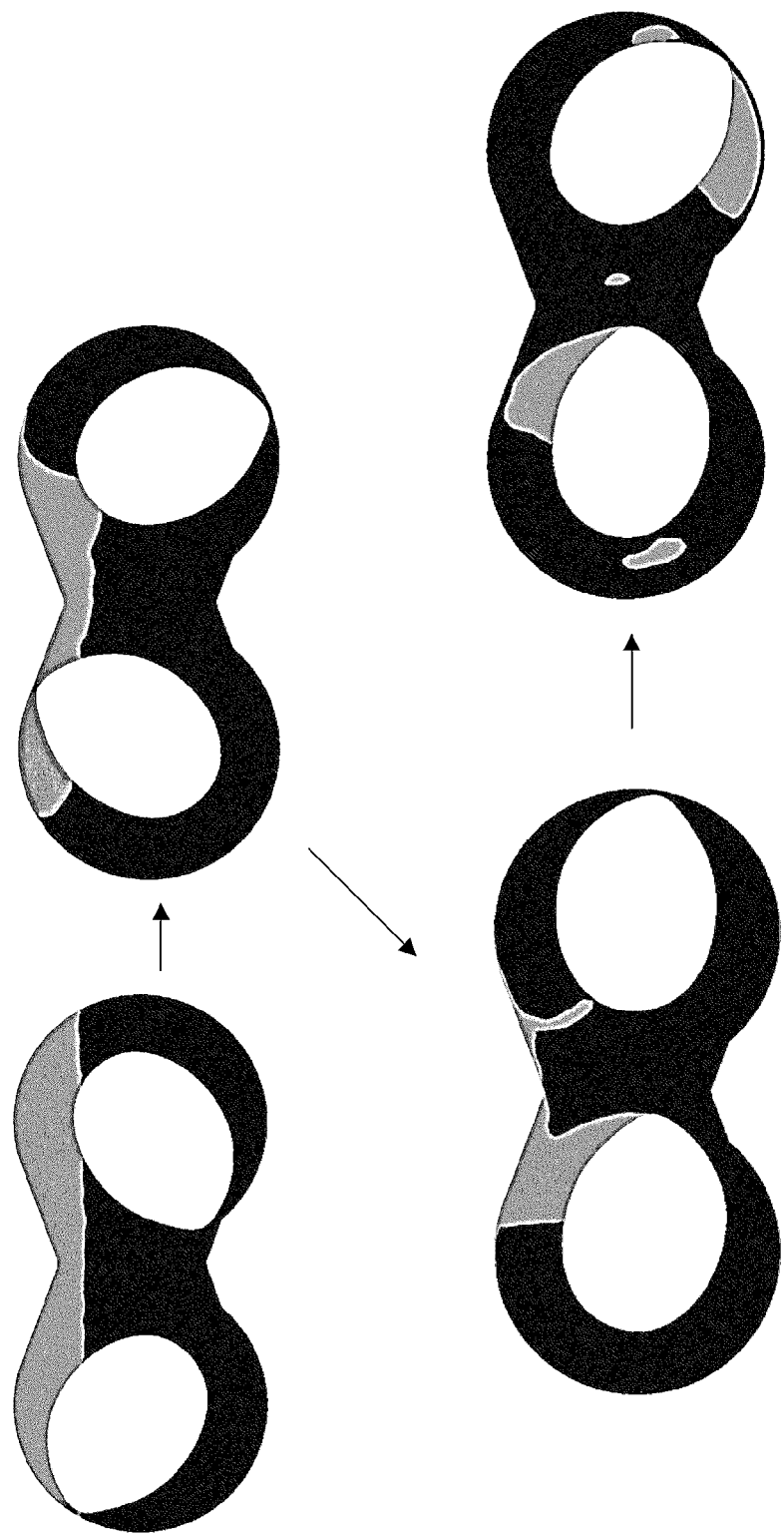
FIG. 10 is a diagram showing kneaded states of the plastic material obtained by the simulation method according to the present invention.

The result of the simulation is shown in FIG. 10, wherein states of the kneaded rubber are shown in the time sequence, the black part is the fluid material model, and the gray part is the gas-phase model.

Meanwhile, according to the method explained in the prior art section of this application, abnormal values occurred frequently during computing the slip velocity, and the flow calculation was not converged.

The invention claimed is:

1. A computer-implemented method for simulating a flow of a high-viscosity fluid in a chamber, comprising steps of:
defining a chamber model of the chamber which is a kneading space defined between a casing and a rotor rotatable disposed in the casing, wherein the shape of the chamber model is varied according to the rotation of the rotor,
defining a fluid material model of the fluid which is a plastic material,
defining physical properties of the plastic material on the fluid material model, wherein the physical properties include at least a shear viscosity,
setting the fluid material model in the chamber model,
defining conditions for carrying out a flow calculation of the fluid material model, wherein the conditions include flow velocity boundary conditions on the wall surface of the chamber model, which include a wall-surface slip condition, which is defined on a contact part of the wall surface with which the fluid material model contacts so that the fluid material model has a slip velocity "$v_{slip}$" in the contact part during the flow calculation,
wherein
the slip velocity "$v_{slip}$" is a velocity of the fluid material model in a direction parallel with the contact surface and defined by the following conditional expression (a)

$$v_{slip} = \alpha \cdot v_t + (1-\alpha) \cdot v_{wall} \quad (a)$$

wherein
"$v_t$" is a component of the velocity of the fluid material model in a direction parallel with the contact surface at a position spaced apart from the contact surface by a distance "$d_{wall}$" normally thereto,
"$v_{wall}$" is a component of a velocity of the contact surface in a direction parallel with the contact surface, and
"$\alpha$" is a slip ratio as a variable from 0 to 1 defined so as to satisfy the following conditional expression (b) or alternatively (c)

$$\alpha/(1-\alpha) = \mu/(d_{wall} \cdot F_{slip}) \quad (b)$$

$$\alpha/(1-\alpha) = \mu/\{(d_{wall} \cdot F_{slip} | v_{slip} - v_{wall} |^{eslip-1}\} \quad (c)$$

wherein
"$\mu$" is the viscosity of the fluid material model,
"$F_{slip}$" is an invariable, and
"$e_{slip}$" is an invariable, and performing the flow calculation to obtain a flow state of the fluid material model due to the variation of the shape of the chamber model, and displaying the flow states of the fluid material model.

2. The method according to claim 1, wherein the values of the "$F_{slip}$" and "$e_{slip}$" are predetermined through an experiment in which a shear stress τw on a wall surface of a space in which the fluid flows, a slip velocity "$_{slip}$" on the wall surface, and a moving velocity "$v_{wall}$" of the wall surface are measured, and then, a double logarithmic chart, in which the slip velocity "$v_{slip}$" is plotted on the X-axis and the shear stress τw is plotted on the Y-axis, is prepared, and a power approximation curve to the plotted points is found as $$y = a \cdot xb$$

and the "$F_{slip}$" and "$e_{slip}$" are determined by the coefficient "a" and the power "b", respectively.

* * * * *